US010481091B2

(12) United States Patent
Varga (10) Patent No.: US 10,481,091 B2
(45) Date of Patent: Nov. 19, 2019

(54) METHOD AND APPARATUS FOR DETECTING HOLES IN SUBSTRATES IN ABSORBENT ARTICLE CONVERTING LINES

(71) Applicant: The Procter & Gamble Company, Cincinnati, OH (US)

(72) Inventor: Stephen Michael Varga, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 305 days.

(21) Appl. No.: 15/421,477

(22) Filed: Feb. 1, 2017

(65) Prior Publication Data
US 2017/0227462 A1    Aug. 10, 2017

Related U.S. Application Data

(60) Provisional application No. 62/291,566, filed on Feb. 5, 2016.

(51) Int. Cl.
*G01J 4/00*    (2006.01)
*G01N 21/59*    (2006.01)
(Continued)

(52) U.S. Cl.
CPC ......... *G01N 21/59* (2013.01); *G01N 21/8806* (2013.01); *G01N 21/8901* (2013.01);
(Continued)

(58) Field of Classification Search
CPC ... G01N 2021/1765; G01N 2021/8822; G01N 2021/8848; G01N 21/59; G01N 21/8806;
(Continued)

(56) References Cited

U.S. PATENT DOCUMENTS 2,075,189 A   3/1937 Galligan
3,025,199 A   3/1962 Harwood
(Continued)

FOREIGN PATENT DOCUMENTS

DE   28 04 975 A1   8/1979
EP    1 022 106 A1   7/2000
(Continued)

OTHER PUBLICATIONS

14202 PCT International Search Report, dated Apr. 11, 2017, 14 pages.

*Primary Examiner* — Sunghee Y Gray
(74) *Attorney, Agent, or Firm* — Charles R. Matson (57) ABSTRACT

The methods herein utilize polarized light for detecting through holes in substrates. A light source directs light through a first polarization filter having a first polarization axis, wherein polarized light travels from the first polarization filter and toward a substrate. The orientation of the polarized light is changed while traveling through substrate material, and is scattered. However, polarized light traveling through a hole in the substrate remains unscattered. A second polarization filter receives unscattered light and scattered light traveling away from the substrate. The second polarization filter includes a second polarization axis angularly offset from and not parallel with the first polarization axis. As such, the second polarization filter blocks the advancement of unscattered light while the scattered light is not blocked by the second polarization filter. The hole is detected based on an absence of unscattered light surrounded by light traveling from the second polarization filter.

5 Claims, 7 Drawing Sheets

(51) Int. Cl.
  *G01N 21/88* (2006.01)
  *G01N 21/956* (2006.01)
  *G01N 33/36* (2006.01)
  *G01N 21/89* (2006.01)
  *G01N 21/894* (2006.01)
  *G01N 21/17* (2006.01)

(52) U.S. Cl.
  CPC ....... *G01N 21/894* (2013.01); *G01N 21/8915* (2013.01); *G01N 21/95692* (2013.01); *G01N 33/36* (2013.01); *G01N 2021/1765* (2013.01); *G01N 2021/8822* (2013.01); *G01N 2021/8848* (2013.01)

(58) Field of Classification Search
  CPC ........... G01N 21/8901; G01N 21/8915; G01N 21/894; G01N 21/95692; G01N 33/36
  USPC ........................................................ 356/370
  See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 4,107,364 A | 8/1978 | Sisson |
| 4,209,563 A | 6/1980 | Sisson |
| 4,515,595 A | 5/1985 | Kievit |
| 4,610,678 A | 9/1986 | Weisman et al. |
| 4,662,875 A | 5/1987 | Hirotsu |
| 4,673,402 A | 6/1987 | Weisman |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany |
| 4,834,741 A | 5/1989 | Sabee |
| 4,845,374 A | 7/1989 | White |
| 4,846,815 A | 7/1989 | Scripps |
| 4,888,231 A | 12/1989 | Angstadt |
| 4,894,060 A | 1/1990 | Nestgard |
| 4,909,803 A | 3/1990 | Aziz |
| 4,940,464 A | 7/1990 | Van Gompel |
| 4,946,527 A | 8/1990 | Battrell |
| 5,092,861 A | 3/1992 | Nomura |
| 5,151,092 A | 9/1992 | Buell |
| 5,167,897 A | 12/1992 | Weber |
| 5,221,274 A | 6/1993 | Buell |
| 5,246,433 A | 9/1993 | Hasse |
| 5,286,543 A | 2/1994 | Ungpiyakul |
| 5,330,458 A | 7/1994 | Buell |
| 5,359,525 A | 10/1994 | Weyenberg |
| 5,360,420 A | 11/1994 | Cook |
| 5,562,646 A | 10/1996 | Goldman |
| 5,569,234 A | 10/1996 | Buell |
| 5,599,335 A | 2/1997 | Goldman |
| 5,628,097 A | 5/1997 | Benson |
| 5,643,588 A | 7/1997 | Roe |
| 5,669,894 A | 9/1997 | Goldman |
| 5,674,216 A | 10/1997 | Buell |
| 5,702,551 A | 12/1997 | Huber |
| 5,735,840 A | 4/1998 | Kline |
| 5,742,392 A | 4/1998 | Anderson |
| 5,897,545 A | 4/1999 | Kline |
| 5,916,661 A | 6/1999 | Benson |
| 5,928,212 A | 7/1999 | Kline |
| 5,957,908 A | 9/1999 | Kline |
| 5,968,025 A | 10/1999 | Roe |
| 6,031,613 A * | 2/2000 | Washington ........... G01D 5/345 356/138 |
| 6,107,537 A | 8/2000 | Elder |
| 6,107,539 A | 8/2000 | Palumbo |
| 6,118,041 A | 9/2000 | Roe |
| 6,120,487 A | 9/2000 | Ashton |
| 6,120,489 A | 9/2000 | Johnson |
| 6,153,209 A | 11/2000 | Vega |
| 6,251,097 B1 | 6/2001 | Kline |
| 6,410,129 B2 | 6/2002 | Zhang |
| 6,426,444 B2 | 7/2002 | Roe |
| 6,432,098 B1 | 8/2002 | Kline |
| 6,545,197 B1 | 4/2003 | Mueller |
| 6,586,652 B1 | 7/2003 | Roe Donald Carroll |
| 6,617,016 B2 | 9/2003 | Zhang |
| 6,627,787 B1 | 9/2003 | Roe |
| 6,650,916 B2 | 11/2003 | Cook |
| 6,669,618 B2 | 12/2003 | Reising |
| 6,790,798 B1 | 9/2004 | Suzuki |
| 6,801,828 B2 | 10/2004 | Popp |
| 6,820,022 B2 | 11/2004 | Popp |
| 6,825,393 B2 | 11/2004 | Roe |
| 6,861,571 B1 | 3/2005 | Roe |
| 7,123,981 B2 | 10/2006 | Dollevoet |
| 8,145,343 B2 | 3/2012 | Debruler |
| 8,145,344 B2 | 3/2012 | Debruler |
| 8,244,393 B2 | 8/2012 | Mclaughlin |
| 8,446,578 B2 | 5/2013 | Sugihara |
| 8,531,679 B2 | 9/2013 | Scheiner |
| 2002/0162776 A1* | 11/2002 | Hergeth ............ A61F 13/15577 209/580 |
| 2003/0233082 A1 | 12/2003 | Kline |
| 2004/0038789 A1* | 2/2004 | Succi ...................... B65B 41/18 493/29 |
| 2004/0097895 A1 | 5/2004 | Busam et al. |
| 2004/0158212 A1 | 8/2004 | Ponomarenko et al. |
| 2005/0195411 A1 | 9/2005 | Alexander et al. |
| 2007/0078427 A1 | 4/2007 | Raycheck |
| 2007/0093769 A1 | 4/2007 | Kline |
| 2008/0235940 A1* | 10/2008 | Jacobsen ................. H01L 24/95 29/832 |
| 2009/0312730 A1 | 12/2009 | LaVon |
| 2013/0072887 A1 | 3/2013 | Lavon |
| 2013/0211356 A1 | 8/2013 | Nishikawa |
| 2013/0306226 A1 | 11/2013 | Zink |

FOREIGN PATENT DOCUMENTS

| | | |
|---|---|---|
| EP | 1 528 907 B1 | 9/2008 |
| JP | H06 18445 A1 | 1/1994 |
| JP | H11 160250 A | 6/1999 |
| JP | 2000 088534 A | 3/2000 |

* cited by examiner

METHOD AND APPARATUS FOR DETECTING HOLES IN SUBSTRATES IN ABSORBENT ARTICLE CONVERTING LINES

FIELD OF THE INVENTION

The present disclosure relates to systems and methods for manufacturing disposable absorbent articles, and more particularly, systems and methods utilizing polarized light to detect through holes in substrates in absorbent article converting lines.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Once the desired component parts are assembled, the advancing web(s) and component parts are subjected to a final knife cut to separate the web(s) into discrete diapers or other absorbent articles. The discrete diapers or absorbent articles may also then be folded and packaged.

For purposes of web control and/or monitoring purposes, absorbent article converting lines may utilize various types of sensor technology to obtain various types of inspection data relating to continuous webs and discrete components added to the webs along the converting line as absorbent articles are constructed therefrom. Example sensor technology may include vision systems, photoelectric sensors, proximity sensors, laser or sonic distance detectors, and the like. Sensor data may be communicated to a controller in various ways. In turn, the controller may be programmed to receive sensor data and report and/or store such data as well as make adjustments to manufacturing processes.

In some manufacturing processes, illuminating optical systems and cameras are arranged adjacent converting lines in order to communicate data to the controller relating to surface topographies of advancing webs and components. In some optical systems, a light source may be used to illuminate a surface of an advancing substrate, wherein light reflected from the substrate is detected by a camera. The light emitted from the light source may also be linearly polarized such that the camera can ascertain information relating to surface features of the substrate by detecting polarized and depolarized light reflected from the substrate surface. Although such optical systems that rely on the detection of reflected polarized light may be able to detect certain anomalies on substrates having relatively smooth surfaces, these systems may not work as well with substrates having relatively rough surfaces, such as nonwovens. In addition, optical systems that rely on detecting polarized light reflected from a substrate surface may not be well suited to detect through holes in substrates, because at acute angles light would not pass through holes due to either the caliper of the substrate or height deviations caused by wrinkles or web flutter; or at perpendicular angles, light from such systems would merely pass through the holes rather than being reflected, confusing holes with surface features which scatter or absorb light such as bond patterns, graphics, or non-uniform basis weights or particulates. As such, some systems utilized to detect through holes in substrates may be configured to illuminate a surface of a substrate and detect light passing through holes in the substrate. Thus, the systems may rely on the detection of relatively bright light as an indication of a through hole in a substrate. However, such systems may have difficulties in detecting through holes in relatively thin and/or translucent material as light traveling through the holes and the substrate may both appear relatively bright, making it hard to discern the existence, locations, and/or perimeters of the holes.

Consequently, it would be beneficial to configure and utilize optical inspection systems that are able to detect and track the locations of through holes in continuous substrates or discrete substrates that may be advancing at relatively high production speeds.

SUMMARY OF THE INVENTION

The present disclosure relates to methods and apparatuses for detecting through holes in substrates with polarized light. As discussed herein, a light source directs light through a first polarization filter having a first polarization axis, wherein polarized light travels from the first polarization filter and toward a first surface of a substrate. In turn, the orientation of the polarized light traveling through substrate material changes, and thus is scattered. In contrast, polarized light traveling through a hole in the substrate does not contact any substrate material, and as such, remains unscattered. The apparatus also includes a second polarization filter positioned to receive unscattered light and scattered light traveling away from the substrate. The second polarization filter includes a second polarization axis that is angularly offset from and not parallel with the first polarization axis of the first polarization filter. Thus, the second polarization filter blocks the advancement of some or all the unscattered light while the scattered light travels through the second polarization filter. A sensor positioned to receive the light traveling from the second polarization filter detects the hole in the substrate based on an absence of unscattered that is surrounded by light traveling from the second polarization filter.

In one form, a method for inspecting a substrate comprises the steps of: advancing a substrate in a machine direction, the substrate having a first surface and an opposing second surface, and defining a width in a cross direction; polarizing light by passing light from a light source through a first polarization filter, wherein the first polarization filter comprises a first polarization axis; directing polarized light from the first polarization filter toward the first surface of the substrate, wherein polarized light traveling through substrate material from the first surface to the second surface is scattered, and wherein polarized light traveling through a hole extending completely through the substrate is unscattered; providing a sensor to detect light traveling from the substrate; blocking unscattered light traveling from the hole in the substrate to the sensor with a second polarization filter, wherein the second polarization filter comprises a second polarization axis is angularly offset from the first polarization axis; and detecting light passing through the second polarization filter with a sensor.

In another form, a method for inspecting a substrate comprises the steps of: providing a substrate, the substrate having a first surface and an opposing second surface; directing light from a light source through a first polarization filter, wherein the first polarization filter comprises a first polarization axis; directing polarized light from the first polarization filter toward the first surface and through the substrate such that scattered light and unscattered light travel through the substrate and away from the second surface of the substrate; positioning a second polarization filter to receive the scattered light and the unscattered light, the second polarization filter comprising a second polarization axis that is nonparallel with the first polarization axis, wherein the scattered light travels through the second polarization filter to a sensor, and wherein the second polarization filter substantially blocks polarized light from traveling to the sensor; and detecting light traveling from the second polarization filter with the sensor.

In yet another form, an apparatus for detecting through holes in a substrate advancing in a machine direction, the substrate having a first surface and an opposing second surface, and defining a width in a cross direction, comprises: a first polarization filter, wherein the first polarization filter comprises a first polarization axis; a light source oriented to direct light through the first polarization filter and toward the first surface of the substrate and through the substrate such that scattered light and unscattered light travel away from the second surface of the substrate; a second polarization filter positioned to receive unscattered light and scattered light traveling away from the second surface of the substrate, the second polarization filter comprising a second polarization axis nonparallel with the first polarization axis, wherein the second polarization filter blocks the advancement of unscattered light and wherein the scattered light travels through the second polarization filter; and a sensor positioned to detect light traveling from the second polarization filter.

DETAILED DESCRIPTION OF THE INVENTION

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. ⅒ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The present disclosure relates to methods and apparatuses for monitoring substrates that may be advancing along a converting apparatus in a machine direction, and more particularly, for detecting through holes in substrates with polarized light. The substrate may include a first surface and an opposing second surface, and a first longitudinal side edge and a second longitudinal side edge separated from the first longitudinal side edge in a cross direction. An apparatus for inspecting the substrate may include a light source oriented to direct light through a first polarization filter having a first polarization axis, wherein the light traveling from the first polarization filter is polarized in a particular orientation. Polarized light traveling from the first polarization filter is directed toward the first surface of the substrate. As such, the orientation of the polarized light traveling through substrate material from the first surface to the second surface of the substrate changes, and thus is scattered or disoriented. Polarized light traveling through a hole extending completely through the substrate from the first surface to the second surface does not contact any substrate material, and as such, is unscattered and remains oriented with the first polarization axis. Thus herein, unscattered light is light that remains polarized in the orientation from first polarization filter. The apparatus also includes a second polarization filter positioned to receive unscattered light and scattered light traveling away from the second surface of the substrate. The second polarization filter includes a second polarization axis that is angularly offset from and not parallel with the first polarization axis. In some configurations, the second polarization axis may be orthogonal or substantially orthogonal with respect to the first polarization axis. Thus, the second polarization filter blocks the advancement of some or all the unscattered light while the scattered light travels through the second polarization filter. The apparatus also includes a sensor positioned to detect the light traveling from the second polarization filter. In turn, the sensor detects the hole in the substrate based on an absence of unscattered or polarized light that is surrounded by the detected scattered light traveling from the second polarization filter.

Figure 1A:
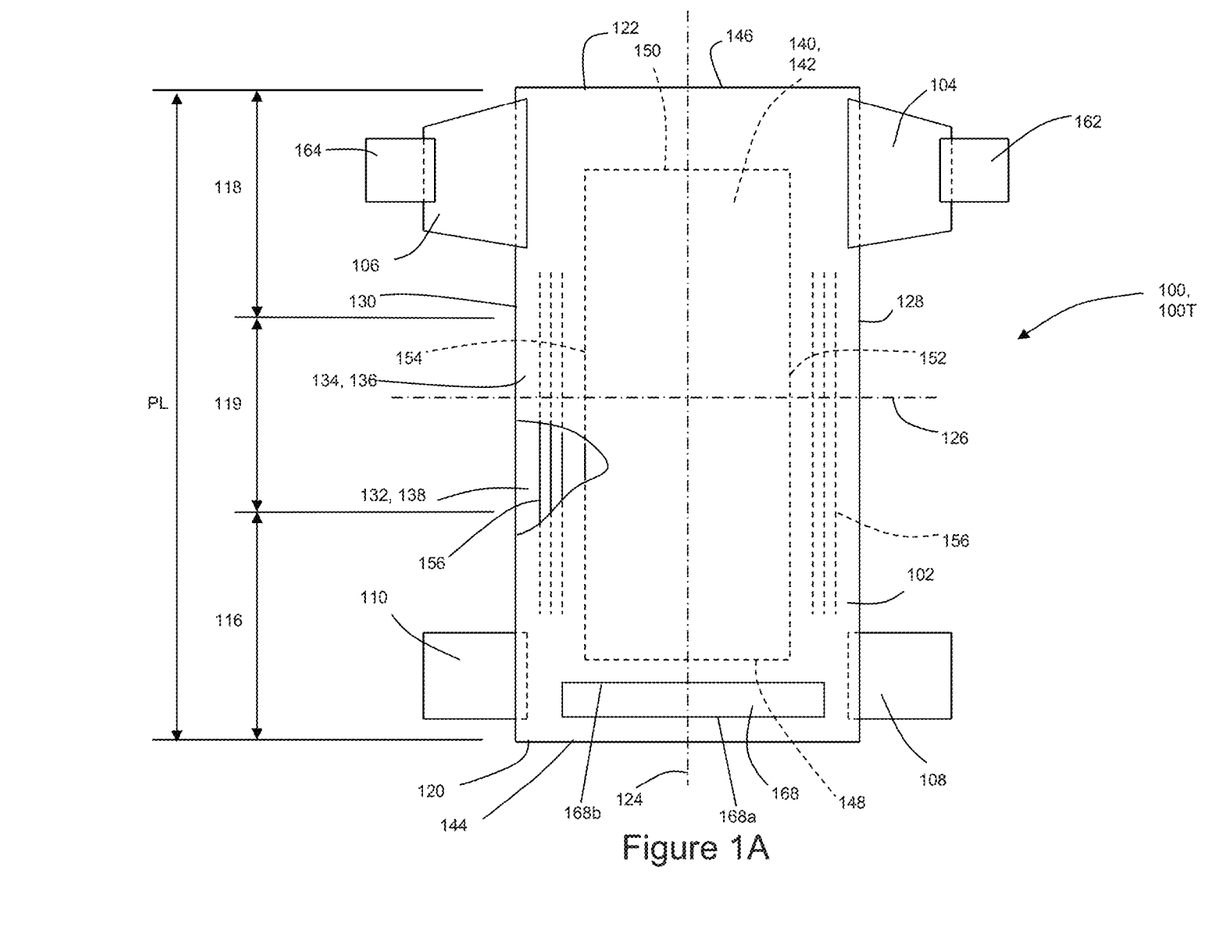
FIG. 1A is a partially cut away plan view of an absorbent article in the form of a taped diaper that may include one or more substrates monitored and/or controlled in accordance with the present disclosure with the portion of the diaper that faces away from a wearer oriented towards the viewer.
Figure 1B:
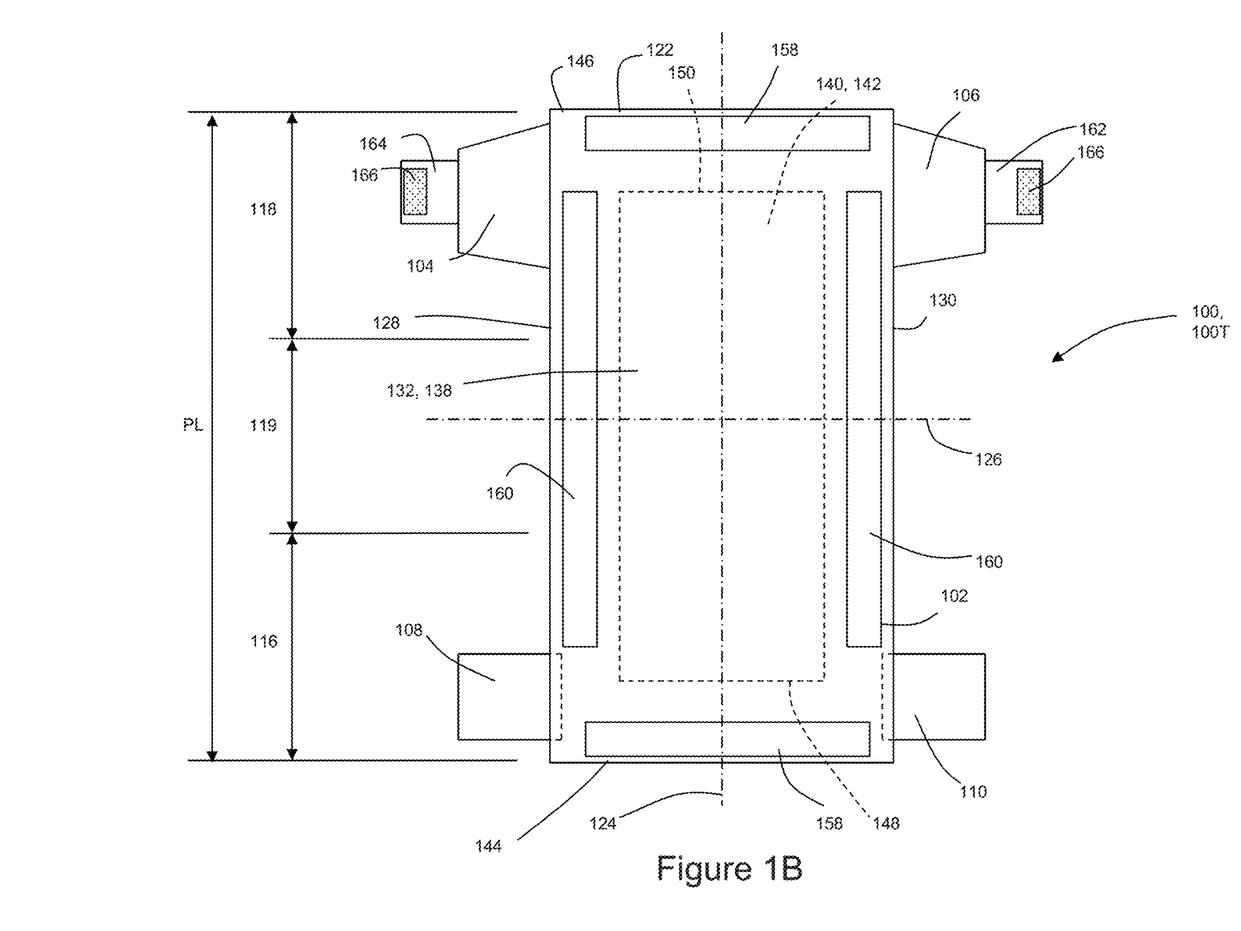
FIG. 1B is a plan view of the absorbent article of FIG. 1A that may include one or more substrates monitored and/or controlled in accordance with the present disclosure with the portion of the diaper that faces toward a wearer oriented towards the viewer.

It is to be appreciated that the systems and methods disclosed herein are applicable to work with various types of converting processes and/or machines, such as for example, absorbent article manufacturing, packaging, and/or printing processes, including processes for manufacturing, packaging, and/or printing feminine hygiene articles, for example pads, pantiliners, and tampons; disposable diapers; incontinence articles, for example pads, adult diapers; homecare articles, for example wipes, pads, towels; and beauty care articles, for example pads, wipes, and skin care articles, such as used for pore cleaning; and wound care articles. The methods and apparatuses are discussed below in the context of manufacturing diapers. And for the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes a chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 100 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092. In some embodiments, the elasticized waistbands 158 may include materials that have been "prestrained" or "mechanically prestrained" (subjected to some degree of localized pattern mechanical stretching to permanently elongate the material). The materials may be prestrained using deep embossing techniques as are known in the art. In some embodiments, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

As shown in FIG. 1B, the chassis 102 may include longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, wherein the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e., toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphrodidic fasteners, and the like. Some examples of fastening systems and/or fastening members 162, 164 are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/0078427 and 2007/0093769.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings.

It is to be appreciated that the connection zone may be constructed from a separate substrate that is connected with the chassis 102 of the taped diaper, such as shown in FIG. 1A. As such, the connection zone 168 may have a pitch length PL defined by a distance extending between a first lateral end edge 168a and the second lateral end edge 168b. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212.

Figure 2A:
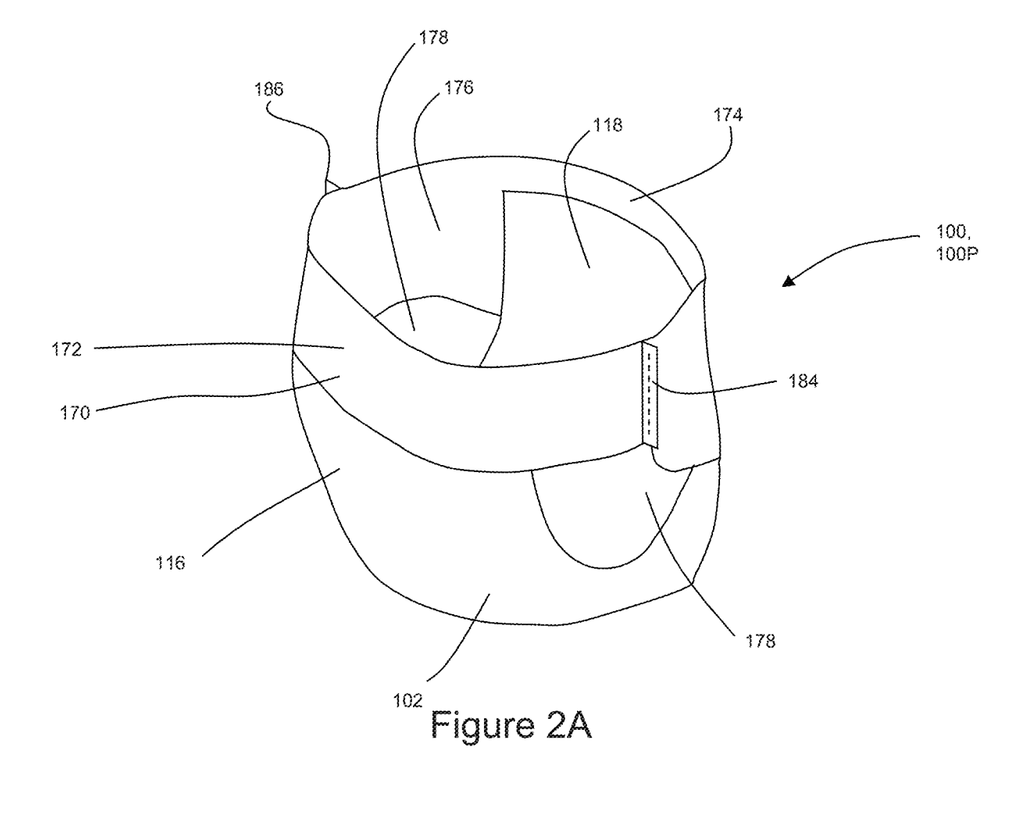
FIG. 2A is a front perspective view of an absorbent article in the form of a diaper pant that may include one or more substrates monitored and/or controlled in accordance with the present disclosure.
Figure 2B:
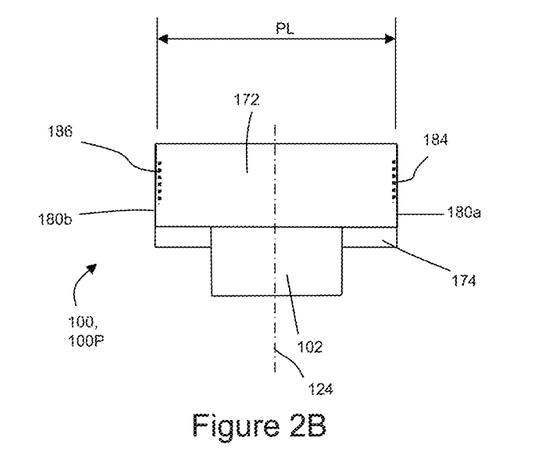
FIG. 2B is a front view of the absorbent article of FIG. 2A.
Figure 2C:
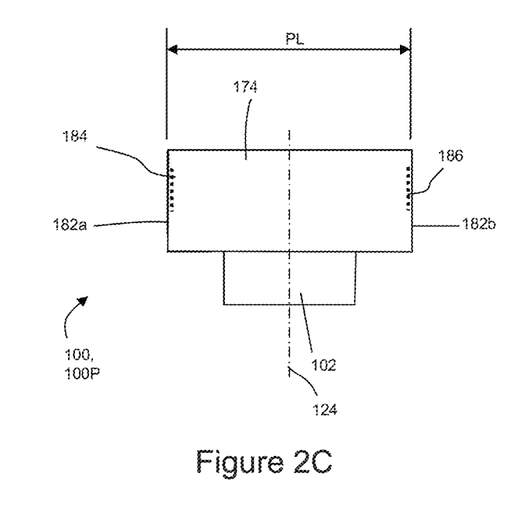
FIG. 2C is a rear view of the absorbent article of FIG. 2A.

As previously mentioned, absorbent articles 100 may also be configured as diaper pants 100P having a continuous perimeter waist opening and continuous perimeter leg openings. For example, FIG. 2A shows a perspective view of an absorbent article 100 in the form of a diaper pant 100P in a pre-fastened configuration, and FIGS. 2B-2C show front and rear plan views of the diaper pant 100P. The diaper pant 100P may include a chassis 102 such a discussed above with reference to FIG. 1A and a ring-like elastic belt 170 such as shown in FIG. 2A. In some embodiments, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178 such as shown in FIG. 2A.

As previously mentioned, the ring-like elastic belt 170 may be defined by a first elastic belt 172 connected with a second elastic belt 174. As shown in FIGS. 2A-2C, the first elastic belt 172 extends between a first longitudinal side edge 180a and a second longitudinal side edge 180b. And the second elastic 174 belt extends between a first longitudinal side edge 182a and a second longitudinal side edge 182b. The distance between the first longitudinal side edge 180a and the second longitudinal side edge 180b defines a pitch length, PL, of the first elastic belt 172, and the distance between the first longitudinal side edge 182a and the second longitudinal side edge 182b defines the pitch length, PL, of the second elastic belt 174. The first elastic belt is connected with the first waist region 116 of the chassis 102, and the second elastic belt 108 is connected with the second waist region 116 of the chassis 102. As shown in FIGS. 2A-2C, opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

As previously mentioned, absorbent articles may be assembled with various substrates that may be inspected during assembly. Thus, in the context of the previous discussion, the apparatuses and methods herein may be used to inspect substrates and components during the manufacture of an absorbent article 100. For example, the apparatuses and methods herein may be utilized to detect through holes in any of the topsheet 138; backsheet 136; absorbent core 140; leg cuffs 156; waist feature 158; side panels 104, 106, 108, 110; connection zones 168; fastening elements 162, 166, and/or belts during the manufacture of an absorbent article 100. It is to be appreciated that the apparatuses and methods herein may detect the presence of, size, shape, location, orientation, and/or positions of holes in various substrates caused by various process operations carried out on the substrates during a manufacturing process, such as for example, high pressure bonding, the application of hot adhesives; ring-roll activation, and others.

Figures 3A, 5:
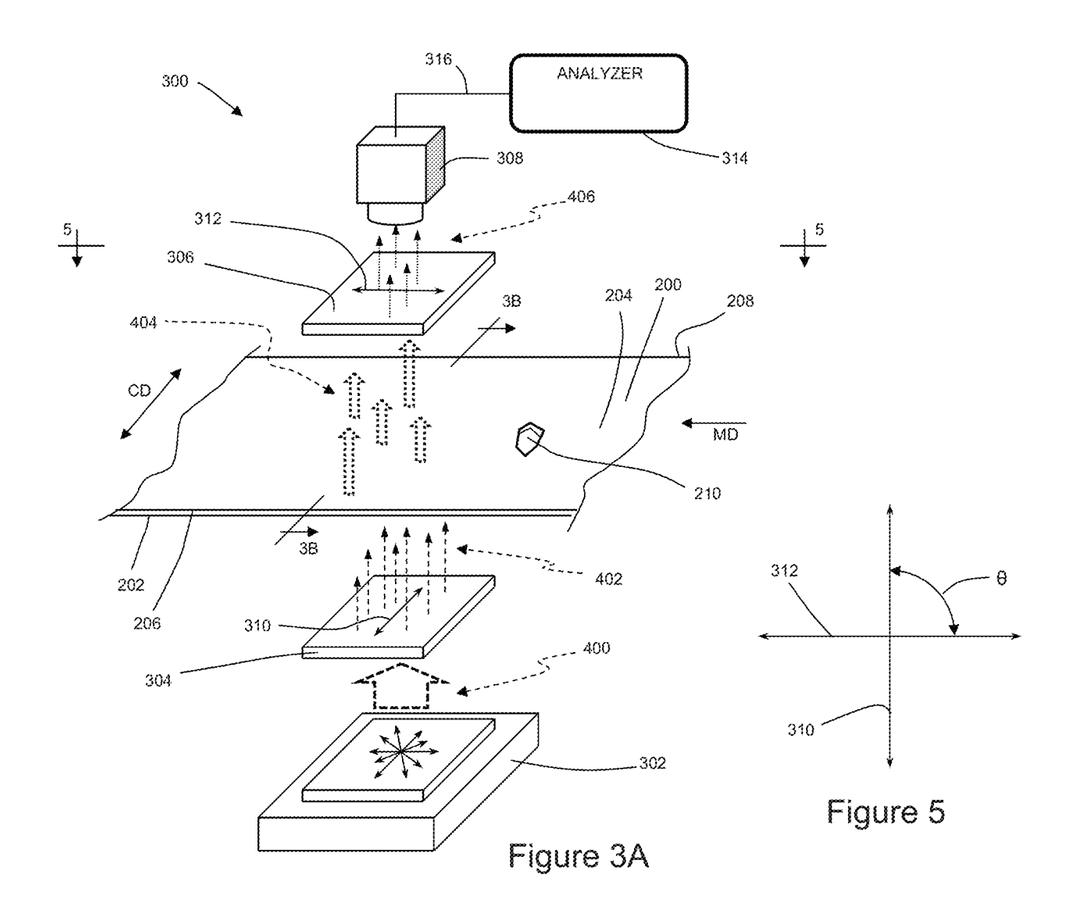
FIG. 3A is a schematic isometric view of an inspection system for detecting through holes in a substrate.
FIG. 5 is a top side view of the inspection system showing only the angular orientation of the first polarization axis relative to the second polarization axis taken along the sectional line 5-5 of FIGS. 3A and 4A.
Figure 3B:
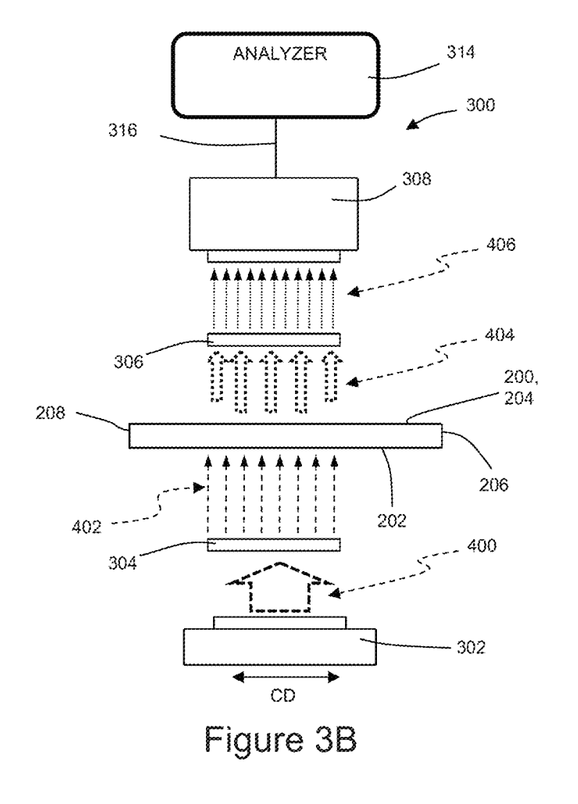
FIG. 3B is a side view of the inspection system and advancing substrate taken along the sectional line 3B-3B of FIG. 3A.

As previously mentioned, the systems and methods disclosed herein are applicable to work with various types of converting processes and/or machines. For example, FIGS. 3A and 3B show schematic representations of a converting process including an inspection apparatus or system 300 for inspecting a substrate 200 advancing in a machine direction MD. The substrate 200 may be continuous substrate or a discrete part and may include a first surface 202 and an opposing second surface 204, and a first longitudinal side edge 206 and a second longitudinal side edge 208 separated from the first longitudinal side edge 206 in a cross direction CD. It is to be appreciated that the substrate 200 may be subject to additional manufacturing operations, such as combining and/or cutting operations, during assembly of a product.

As shown in FIGS. 3A and 3B, the substrate 200 may also include one or more holes 210 that extend completely through the substrate 200 as well as the first surface 202 and the second surface 204. As such, the inspection system 300 may be configured to detect holes 210 in the advancing substrate 200. It is to be appreciated that existence of holes 210 in the substrate 200 may exist for various reasons. For example, the existence of the holes 210 may be the result of an unintended defect in the manufacture or handling of the substrate 200, or an intended or unintended result subjecting the substrate 200 to a converting or manufacturing operation, or both. In turn, the inspection system 300 may also be configured to detect and communicate the existence of such holes 210 and/or make desired adjustments to manufacturing operations involving the advancing substrate 200. For example, the inspection system 300 may utilize perform alarming and/or reject functions base on hole detections. In other examples, various assembly operations may utilize hole size, shape, orientation, and/or position to carry out such operations, such as for example, operations that involve placement or application of other components on the substrate 200, such as fluids intended to be applied adjacent the holes 210.

With continued reference to FIGS. 3A and 3B, the inspection system 300 may be configured to interact with, monitor, and/or control a converting line. In some configurations, the inspection system 300 may include a light source 302, a first polarization filter 304, a second polarization filter 306, and a sensor 308. As discussed in more detail below, the first polarization filter 304 includes a first polarization axis 310, and the second polarization filter 306 includes a second polarization axis 312, wherein second polarization axis 312 is angularly offset from and nonparallel with the first polarization axis 310. As discussed in more detail below with reference to FIGS. 3A-4B, the first polarization filter 304 polarizes light 400 from the light source 302 in a particular orientation. In turn, polarized light 402 is directed toward the substrate 200. The orientation of the polarized light 402 is changed and is scattered and disoriented while traveling through the material of the substrate 200. As such, the scattered light 404 travels away from the substrate 200, through the second polarization filter 306, and light 406 traveling from the second polarization filter 306 is detected by the sensor 308. It is to be appreciated that the light 406 traveling away from the second polarization filter 306 has been polarized by the second polarization filter 306. In contrast, when polarized light 402 is directed toward the substrate 200 in a region where a hole 210 is located, the orientation of the polarized light 402 traveling from the first polarization filter 304 passes directly through the hole 210 in the substrate 200 remains unchanged without being scattered, while the orientation of the polarized light 402 traveling through the material of substrate 200 changes in the area surrounding the hole 210 and therefore is scattered. Because the second polarization axis 312 is angularly offset from the first polarization axis 310, the second polarization filter 306 blocks unscattered or polarized light 402 that has traveled through the hole 210, while the scattered light 404 travels through the second polarization filter 306. In turn, the sensor 308 detects the hole 210 in the substrate 200 based on the absence of light 402 passing through the second polarization filter 306 that is surrounded by detected light 406 traveling from the second polarization filter 306.

It is to be appreciated that inspection systems 300 and methods herein may include one or more light sources 302 configured in various ways. For example, in some embodiments, the light source 302 may include line lights such as light emitting diode (LED) line lights. Examples of such lights include the ADVANCED ILLUMINATION IL068, various line lights available from METAPHASE, various line lights available from VOLPI such as model number 60023, as well as various line lights available from CCS AMERICA, INC. Other example light source 302 configurations may include halogen or other sources coupled to fiber bundles. For example, halogen sources may include those available from SCHOTT and fiber bundles and/or panels may include those available from SCHOTT and/or FIBEROPTICS TECHNOLOGY INC. In addition, the light source 302 may be configured to emit light in any suitable frequency range including, for example, visible, ultra-violet, and/or infrared.

It is to be appreciated that various different types of sensors 308 may be used with the inspection systems 300 and methods herein. For example, sensors 308 may be configured as photo-optic sensors that receive light 406 and serve to determine the presence or absence of a hole in the substrate 200. Sensors 308 may also be configured as vision systems and other sub-processing devices to perform detection and, in some cases, logic to more accurately determine the status of an inspected product. Particular examples of such sensors 308 may include Cognex Insight, DVT Legend or Keyence smart cameras, component vision systems such as National Instruments PXI or PC based vision system such as Cognex VisionPro or any other vision system software which can run on a PC platform. Based on the ability to detect light 406 as discussed above, the sensors 308 may be configured to detect the presence or absence of through holes 210 in substrates, and may be configured to detect the sizes, shapes, orientations, positions, and/or relative placements of such holes on substrates.

As shown in FIGS. 3A and 3B, the sensor 308 and/or second polarization filter 306 may be arranged adjacent the advancing substrate 200, and the sensor 308 may communicate with an analyzer 314. Based on such communications, the analyzer 314 may monitor and affect various operations on a converting line. For example, the analyzer 314 may send various types of control commands to the converting line based on communications with the sensor 308. In some embodiments, the control commands may be in the form of commands to: reject certain portions of the substrate and/or products made with the substrate; control the deposition of various components on the substrate 200, such as adhesives or ink; and/or increase or decrease substrate 200 advancement speeds and/or commands to reposition the substrate 200 in cross direction CD.

It is to be appreciated that the analyzer 314 may be configured in various ways. For example, the analyzer 314 may be in the form of a personal computer (PC), a central processing unit (CPU), a field programmable gate array (FPGA), an application specific integrated circuit (ASIC), or a graphical processing unit (GPU). FPGA examples may include the National Instruments PCIe-1473R, National Instruments PXIe-1435, National Instruments 1483R with FlexRIO FPGA module, Altera Stratix II, Altera Cyclone III, Xilinx Spartan 6, Xilink Vertex 6 or Vertex 7. GPU examples may include GeForce GTX 780 (Ti), Quadro K6000, Radeon R9 295X2 and Radeon HD 8990.

It is to be appreciated that the analyzer 314 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. Process and product data may be stored directly in the aforementioned computer systems or may be located in a separate data historian. In some embodiments, the historian is a simple data table in the controller. In other embodiments, the historian may be a relational or simple database. Example historian applications include Rockwell Automation Factory Talk Historian, General Electric Proficy Historian, OSI PI, or any custom historian that may be configured from Oracle, SQL or any of a number of database applications. It is also to be appreciated that the analyzer 314 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907 B1, all of which are incorporated by reference herein.

As shown in FIGS. 3A and 3B, the analyzer 314 may be in communication with the sensor 308 through a communication network 316. As such, it is to be appreciated that the analyzer 314 may be physically located near the advancing substrate 200 and/or sensor 308 and/or may be located at another location and in communication with the sensor 308 via a wired and/or wireless network 316. In some embodiments, the communication network 316 is configured as a non-deterministic communication network, such as for example, Ethernet or Ethernet IP (industrial protocol) communication network.

It is to be appreciated that the sensor light source 302, first polarization filter 304, second polarization filter 306, and/or sensor 308 may be configured and arranged in various ways relative to substrates 200 that are being monitored. In some embodiments, light 400 from the light source 400 and/or polarized light 402 from the first polarization filter 304 may be directed to the substrate 200 from various locations and/or various directions with or without the use of mirrors and/or lenses. In addition, scattered light 404 and/or polarized light 402 traveling away from the substrate 200 may be directed to the second polarization filter 306 and/or sensor 308 in various locations and/or various directions with or without the use of mirrors and/or lenses. In some embodiments, the light source 302, first polarization filter 304, second polarization filter 306, and/or sensor 308 may be telecentrically arranged.

For example, FIGS. 3A and 3B shows the inspection system 300 wherein the light source 302 is oriented to direct light 400 through the first polarization filter 304, which polarizes the light 400 from the light source 302. As such, polarized light 402 travels from the first polarization filter 304 and toward the first surface 202 of the substrate 200. The polarized light 402 may be directed travel at a 90 degree angle with respect to the first surface 202 of the substrate 200. As the polarized light 402 travels from the first surface 202, through the substrate 200, and to the second surface 204, the polarized light 402 may be reflected and/or scattered by the substrate material so as to change the orientation of the polarized light, and thus is converted to scattered light 404. It is to be appreciated that light 404 as referred to herein also includes polarized light 402 that is reflected by the substrate material so as to remain polarized but has a changed angle of polarization. The scattered light 404 then travels away from the second surface 204 of the substrate 200 and through the second polarization filter 306. In turn, the sensor 308 is positioned to detect the light 406 traveling away from the second polarization filter 306.

Figure 4A:
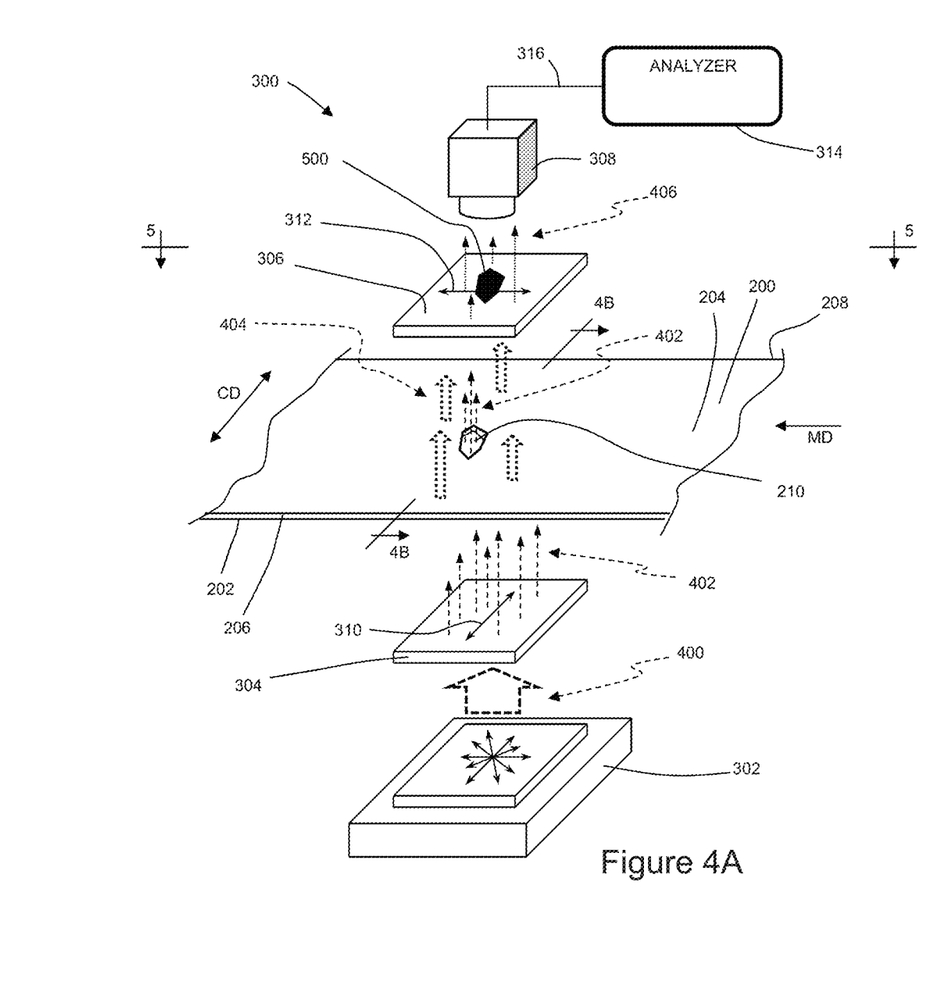
FIG. 4A is a schematic isometric view of the inspection system of FIG. 3A wherein polarized light travels through a hole in the substrate and wherein a second polarization filter blocks polarized light traveling from the substrate.
Figure 4B:
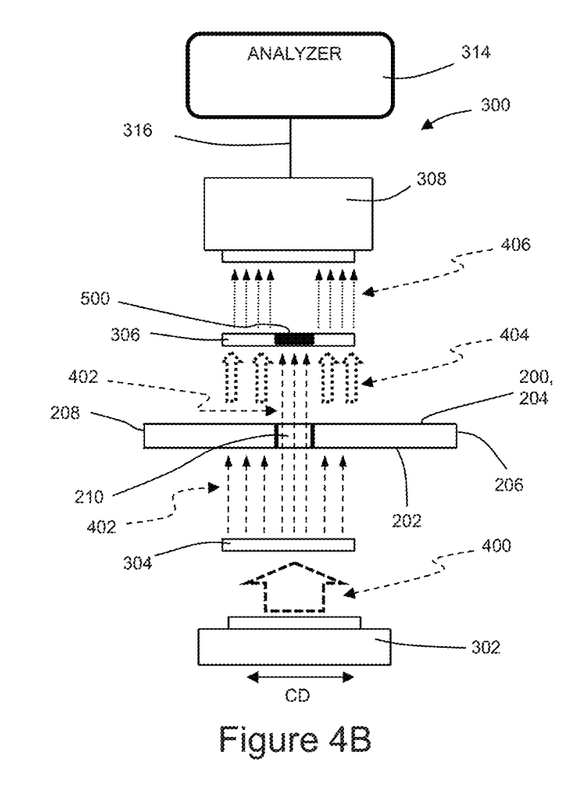
FIG. 4B is a side view of the inspection system and advancing substrate taken along the sectional line 4B-4B of FIG. 4A.

As shown in FIGS. 3A and 3B, the substrate 200 may include a through hole 210. Thus, as the substrate advances the machine direction MD, the hole 210 also advances in the machine direction MD to a position where the polarized light 402 travels through the hole 210 without being scattered. For example, as shown in FIGS. 4A and 4B, the hole 210 has advanced in the machine direction to a position where the polarized light 402 from the first polarization filter 304 is directed toward a region of the first surface 202 of the substrate 200 where the hole 210 is located. Because the hole 210 extends completely through the substrate 200 from the first surface 202 to the second surface 204, the polarized light 402 traveling from the first polarization filter 304 travels directly through the hole 210 in the substrate 200 without colliding with substrate material, and thus, the polarized light 402 traveling through the hole 210 is not scattered and remains polarized in the same orientation. In turn, the orientation of polarized light 402 changes as the polarized light 402 travels through and/or collides with the material of substrate 200 in the area surrounding the hole 210 and becomes scattered light 404 after being reflected and/or scattered by the substrate material. As mentioned above, the second polarization axis 312 is angularly offset from the first polarization axis 310, some or all the unscattered or polarized light 402 traveling through the hole 210 and away from the second surface 204 is blocked or prevented from traveling through the second polarization filter 306. However, the scattered light 404 traveling away from the second surface 204 outside a perimeter of the hole 210 travels through the second polarization filter 306. In turn, the presence of the hole 210 results in unscattered or polarized light 402 being blocked by the second polarization filter 306, which is represented by the darkened region 500 in the second polarization filter 306 shown in FIGS. 4A and 4B. As such, the sensor 308 detects the hole 210 in the substrate 200 by detecting the light 406 that surrounds the darkened region 500 created by the unscattered or polarized light 402 that is blocked from passing through the second polarization filter 306.

As previously mentioned, the second polarization axis 312 of the second polarization filter 306 is not parallel with and is angularly offset from the first polarization axis 310 of the first polarization filter 304. For example, FIG. 5 is a top side view of the inspection system 300 showing the angular orientation of the first polarization axis 310 relative to the second polarization axis 312 taken along the sectional line 5-5 of FIGS. 3A and 4A. As shown in FIG. 5, the first polarization axis 310 may be angularly offset from the second polarization axis 312 by an angle θ. It is to be appreciated that a maximum percentage of polarized light 402 may be blocked by the second polarization filter 306 when the angle θ is 90 degrees, and lesser percentages of polarized light 402 may be blocked by the second polarization filter 306 as the angle θ is decreased (or increased) from 90 degrees. As such, it is to be appreciated in various configurations of the inspection system 300, second polarization axis 312 and first polarization axis 310 can be angularly oriented to define angles θ that are greater than 0 degrees and equal to or less than about 90 degrees, or define angles θ that are less than 180 degrees and equal to or greater than about 90 degrees. For example, the second polarization axis 312 may be orthogonal or substantially orthogonal with respect to the first polarization axis 310 such that the angle θ is equal to 90 degrees or about 90 degrees.

It is to be appreciated that in some system configurations, the angle θ may be deviated from 90 degrees such that the second polarization filter 306 blocks less than 100% of the polarized light 402 that has traveled through the hole 210, and wherein the second polarization filter 306 blocks enough of the polarized light 402 to still enable the sensor 308 to detect a hole 210 based on a contrast between the light 406 traveling from the second polarization filter 306 and the partially blocked polarized light 402. As such, the amount that the angle θ may be deviated from 90 degrees may be based on translucency of the substrate 200 and the desired contrast between polarized light 402 blocked by the second polarization filter 306 and the light 406 traveling from the second polarization filter 306. For example, the amount the angle θ may be deviated from 90 degrees can be expressed in the following equation:

$R = \sin^{-1}(T \times C)$, wherein

R=The amount (degrees) the angle θ may be deviated from 90 degrees;

T=The percent of scattered light that is transmitted through the substrate (expressed as a decimal, i.e., 90% is 0.90); and C=The percent of contrast between the hole and the substrate (expressed as a decimal, i.e., 50% is 0.50).

Table 1 below shows example values of R as a function of the translucency of the substrate, assuming a constant value of C at 50%,

TABLE 1

| R (degrees) | T | C |
| --- | --- | --- |
| 28.3 | 0.95 | 0.50 |
| 26.7 | 0.90 | 0.50 |
| 23.6 | 0.80 | 0.50 |
| 20.5 | 0.70 | 0.50 |
| 17.4 | 0.60 | 0.50 |
| 14.5 | 0.50 | 0.50 |
| 11.5 | 0.40 | 0.50 |

TABLE 1-continued

| R (degrees) | T | C |
|---|---|---|
| 8.6 | 0.30 | 0.50 |
| 5.7 | 0.20 | 0.50 |
| 2.9 | 0.10 | 0.50 |

Thus, for example, in some embodiments, the angle θ between the first polarization axis 310 and the second polarization axis 312 may be from 61.7 degrees to 118.3 degrees when the translucency of the substrate 200 is such that 95% of the scattered light 404 passes through the substrate 200, and it is desirable to achieve at least a 50% percent contrast between the hole and the substrate. And in some embodiments, the angle θ between the first polarization axis 310 and the second polarization axis 312 may be from 87.1 to 92.9 when the translucency of the substrate 200 is such that 10% of the scattered light 404 passes through the substrate 200, and it is desirable to achieve at least a 50% percent contrast between the hold and the substrate.

As mentioned above, the inspection system 300 may be configured to interact with, monitor, and/or control a converting line and/or the substrate 200 advancing through the converting line. For example, based on the detections of the sensor 308, feedback signals from the sensor 308 in the form of inspection parameters may be communicated to an analyzer 314. Based on such communications, the analyzer 314 may monitor and affect various operations on the converting line. For example, the analyzer 314 may send various types of control commands to the converting line based on communications with the sensor 308.

It is also to be appreciated that inspection parameters may be provided from the sensor 308 in various forms. In some embodiments, inspection parameters may be in the form of "results," such as for example, provided from a sensor state change resulting in a binary input corresponding with the detected presence or absence of light. For example, inspection parameters may indicate the presence or absence of holes in various locations on a substrates and/or components. In another embodiment, inspection parameters may be provided in the form of measurements and/or numerical indications of detected positions of holes on components and/or substrates; numerical indications of the positions of holes on components and/or substrates relative to other holes and/or other components and/or substrate features; and/or numerical indications of positions holes in components and/or substrates relative to another physical or virtual reference. In some embodiments, measurements may be correlated with quality or performance parameters, such as for example, bond strengths of the adhesives or absorptive performance of an inspected product. In some embodiments, inspection parameters may be in the form of images transferred via a standard protocol such as ftp (File Transfer Protocol), DDE (Dynamic Data Exchange), or OPC (Object Linking and Embedding for Process Control), which are stored in a database or stored in a specified directory on an image server for the purpose of either operator visualization, offline image processing or claim support. Building on the discussion above, inspection parameters may be used to determine various characteristics of components and/or substrates during the assembly process. For example, inspection parameters may indicate the presence of, size, shape, location, orientation, and/or positions of holes caused by various process operations carried out on substrates during an absorbent article manufacturing process.

This application claims the benefit of U.S. Provisional Application No. 62/291,566 filed on Feb. 5, 2016, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling absorbent articles, the method comprising the steps of:
   advancing a substrate in a machine direction, the substrate comprising a nonwoven and having a first surface and an opposing second surface, and defining a width in a cross direction;
   polarizing light by passing light from a light source through a first polarization filter, wherein the first polarization filter comprises a first polarization axis;
   directing polarized light from the first polarization filter toward the first surface of the substrate, wherein polarized light traveling through substrate material from the first surface to the second surface is scattered, and wherein polarized light traveling through a hole extending completely through the substrate is unscattered;
   providing a sensor to detect light traveling from the substrate;
   filtering unscattered light traveling from the hole in the substrate to the sensor with a second polarization filter, wherein the second polarization filter comprises a second polarization axis angularly offset from the first polarization axis; and
   detecting light passing through the second polarization filter with the sensor;
   detecting the hole in the substrate based on an absence of unscattered light traveling from the second polarization filter surrounded by detected scattered light; and
   applying fluid adjacent the hole; and
   converting the substrate into an absorbent article in an absorbent article converting line.

2. The method of claim 1, wherein the step of detecting the hole further comprises detecting at least one of the position, orientation, shape, and size of the hole.

3. The method of claim 1, wherein the second polarization axis is orthogonal to the first polarization axis.

4. The method of claim 1, wherein the polarized light travels in a direction that is 90 degrees with respect to the first surface of the substrate.

5. The method of claim 1, wherein the sensor comprises a camera.

\* \* \* \* \*